United States Patent [19] [11] 4,048,017
Roesler [45] Sept. 13, 1977

[54] INTRODUCTION OF NUTRIENT MEDIUM INTO A FERMENTER

[75] Inventor: Frank Cornelius Roesler, Stockton-on-Tees, England

[73] Assignee: Imperial Chemical Industries Limited, London, England

[21] Appl. No.: 601,494

[22] Filed: Aug. 4, 1975

[30] Foreign Application Priority Data
Aug. 14, 1974 United Kingdom .............. 35754/74
May 19, 1975 United Kingdom .............. 21288/75

[51] Int. Cl.$^2$ ............................................. C12B 1/00
[52] U.S. Cl. ..................................... 195/109; 195/49; 195/115
[58] Field of Search ....................... 195/139, 141–143, 195/115, 117, 49, 28 R, 109; 261/123

[56] References Cited
U.S. PATENT DOCUMENTS
2,822,319 2/1958 Monod .................................. 195/115
3,405,920 10/1968 Lefraneois ........................... 261/123

OTHER PUBLICATIONS
1,370,892 10001974 UK

Primary Examiner—R. B. Penland
Attorney, Agent, or Firm—Cushman, Darby & Cushman

[57] ABSTRACT

A method and apparatus for continuous fermentation wherein a limiting nutrient such as a carbon source is supplied to a culture at sufficient positions and at suitable rates to ensure that another nutrient such as oxygen does not effectively become the limiting nutrient. The invention is particularly applicable to the cultivation of bacteria such as *Pseudomonas methylotropha* upon methanol where it is undesirable that oxygen should become the limiting nutrient in any part of the culture.

5 Claims, 8 Drawing Figures

INTRODUCTION OF NUTRIENT MEDIUM INTO A FERMENTER

This invention relates to the introduction of a nutrient medium into a fermenter and to its distribution within the fermenter.

Many fermentation processes are preferably performed on an industrial scale as continuous processes, nutrient medium comprising a carbon source and sources or organic and/or inorganic nutrients being continuously supplied to a fermenter at a rate substantially the same as that at which culture is removed from the fermenter. The carbon source and the various organic and/or inorganic nutrients may be supplied to the fermenter as separate feeds or all or most of them may be supplied as a single feed. For example ammonia is a suitable nitrogen source and may be supplied to the fermenter as a separate feed, the other inorganic nutrients and the carbon source being supplied as a single feed. In such processes microbial cells are separated from the culture removed from the fermenter and the remaining medium may be combined with fresh nutrients which are being supplied to the fermenter.

In continuous fermentation processes, the culture medium into which an organism is inoculated may be designed such that any of the required nutrients, eg nitrogen, phosphorus, magnesium or iron or the carbon source may be present in such quantities as to be limiting to growth with respect to the other constituents of the medium. This may be used to regulate the growth of the culture. The nutrient present in growth limiting quantities is referred to as the limiting nutrient.

Industrial fermentation processes are preferably performed in large fermenters. In such fermenters the limiting nutrient is supplied to the culture at one or at a small number of possitions such that substantial amounts of the limiting nutrient enter the culture at these positions. Thus in the immediate vicinity of a limiting nutrient addition position the concentration of the limiting nutrient in the culture is greater than it is elsewhere. The possibility then arises that in a region of greater limiting nutrient concentration another nutrient, particularly oxygen in aerobic fermentations, is completely used up by the microorganisms present in the culture before all the designed limiting nutrient is consumed. In such circumstances in this region the other nutrient, eg oxygen in an aerobic fermentation, effectively becomes the limiting nutrient often to the detriment of the growth of the culture. Furthermore, the introduction of large amounts of the limiting nutrient at any given place results in microorganisms present in the vicinity of that place being subjected temporarily to high concentrations of the limiting nutrient. This can be harmful to the microorganisms for example in the process of our UK Specification No. 1,370,892.

According to the present invention we provide a method for the continuous fermentation of a culture comprising a nutrient medium, one of the constituents of which is a growth limiting nutrient, and microorganisms capable of utilizing the medium for growth wherein the growth limiting nutrient is supplied to the culture at sufficient positions and in such amounts at each position that substantially all the limiting nutrient supplied at each position is consumed by the microorganisms present in the culture in the vicinity of that position before another nutrient available to them in the culture in the vicinity of that position is exhausted and becomes the limiting nutrient.

Also according to the invention we provide a fermenter having means for continuously supplying a nutrient medium thereinto, means for continuously removing culture therefrom, the means for supplying nutrient medium thereinto including means whereby a limiting nutrient is supplied to the fermenter at sufficient positions and in such amounts at each position that substantially all the limiting nutrient supplied at each position is consumed by microorganisms present in a culture in the fermenter in the vicinity of that position before another nutrient available to the microorganisms in the vicinity of that position is exhausted and becomes the limiting nutrient.

The fermenter may be any type of fermenter eg a tank wherein circulation of the culture is induced by mechanical stirring or, in the case of an aerobic fermentation, by blowing air thereinto. Preferably it is a fermenter such as those described in our UK Specification No. 1,353,008 or our co-pending UK Applications Nos. 23330/73, 24266/75 and 52430/74 comprising a riser and a downcomer connected at their upper and lower ends and wherein circulation of culture around the system is caused by injecting an oxygen-containing gas such as air into the lower part of the riser. The present invention is very suitable for use in aerobic fermentations and may be usefully employed in bacterial fermentations such as the process of our UK Specification No. 1,370,892 for culturing methanol utilizing strains of bacteria of the species *Pseudomonas methylotropha, Microcyclus polymorphum, Hyphomicrobium variabile* or *Pseudomonas rosea,* cultures of a number of strains of which are available from the National Collection of Industrial Bacteria (NCIB), Torry Research Station, Aberdeen, Scotland, UK - NCIB Nos. 10508-17 and 10592-612.

In aerobic fermentations the invention has the main advantage that it avoids regions developing in the fermenter wherein the culture grows in effective oxygen limitation, ie all the oxygen available to the microorganisms has been used up in a region in which supplies of the limiting nutrient, usually the carbon source are still available. In the specification such regions will be termed regions of "oxygen shadow".

The limiting nutrient is suitably supplied to the fermenter at an average of at least one position per cubic meter of the effective volume of the fermenter, preferably at 3 to 6 positions per cubic meter. By the effective volume of the fermenter we mean that volume which is occupied by the culture and in which gasification of, nutrient utilization by and growth of the microorganisms present in the culture is taking place.

In an apparatus for aerobic fermentation the effective volume for microorganism growth is that part of the volume in which, through mass transfer from gas bubbles, a positive dissolved oxygen tension (partial pressure of oxygen) can be maintained.

In a single tank fermenter the effective volume is effectively the whole volume of the tank occupied by the culture. In a fermenter such as those of our UK Specification No. 1,353,008 or UK Applications Nos. 23330/73, 24266/75 or 52430/74 it comprises the riser of the fermenter and can in some cases include all or part of the downcomer.

The amount of nutrient supplied to the culture at any position is that which corresponds stoichiometrically with the locally available supply of any nutrient such as oxygen which is available to microorganisms present in the culture and the exhaustion of the supply of which, thus making it effectively the limiting nutrient, would be detrimental to the growth of the culture. In an aerobic fermentation the amount of nutrient supplied at any position would usually be that which corresponds stoichiometrically with the amount of oxygen that can be taken up by the culture. In the process of our UK Specification No. 1,370,892 with methanol as the limiting nutrient the amount of methanol supplied through any single dispersing means such as a nozzle or other orifice at any position suitably does not exceed 15 l/hr, being preferably 2 to 6 l/hr. Very suitably the rate of methanol injection from each dispersing means is designed with reference to the local availability of oxygen which will depend on the pressure and hence on the position in the fermenter.

Preferably the methanol is mixed with recycle nutrient medium before being supplied to the fermenter. It is also preferred that the methanol containing medium is supplied to the culture through narrow orifices, eg within the size range 2mm to 6mm diameter at a velocity above 3 meters/sec. especially above 6 meters/sec.

In the apparatus of the invention the limiting nutrient may be supplied to the culture through a wide variety of sparging systems made up of tubes. One suitable arrangement comprises a plurality of substantially vertical tubes distributed within the fermenter at the corners of one or more regular polygons and connected to at least one common source of nutrient medium or limiting nutrient, the wall of each vertical tube being perforated by holes whose frequency varies suitably along the line of flow of upwardly — or downwardly — flowing culture, successive holes in the line of flow being spaced around the circumference of the tube in a regular pattern.

In this arrangement the number of substantially vertical tubes is preferably from 4 to 16 distributed at the corners of one or more coaxial regular figures. These tubes are preferably connected to one or more circular tubes of larger bore which encircle the regular polygon or polygons and are connected to a source of medium containing the limiting nutrient. The vertical tubes may also be connected to a plurality of such circular supply tube systems, eg 3, spaced at regular intervals along the height of the vertical tubes and connected to different supply sources. The circular tubes are preferably positioned at the lower ends of the vertical tubes.

In this arrangement the vertical distance between the levels of successive holes suitably increases upwardly along the direction of flow of culture in the fermenter. However on average there are preferably from 1 to 4 holes per meter of the height of the vertical tubes. Very suitably in the riser of a fermenter of UK Specification No. 1,353,008 or co-pending UK Applications Nos. 23330/73, 24266/75 and 52430/74 which is 50 meters high each vertical tube may contain 50 to 200 holes, especially about 100 holes. For 3 vertically arranged systems the number of holes per tube may suitably be 55, 30 and 15 in the three levels respectively.

When the above arrangement is installed in the riser of a fermenter of UK Specification No. 1,353,008 or our co-pending UK Applications Nos. 23330/73, 24266/75 and 52430/74 if it comprises a single polygon its diameter is preferably between 0.55 and 0.75 times the riser diameter if the riser is cylindrical. When the arrangement comprises two coaxial polygons the diameter of the outer polygon is preferably between 0.4 and 0.65 times that of the riser whilst the diameter of the outer polygon is between 0.65 and 0.9 times. When the riser contains baffles or other internal fittings these are preferably arranged to present no obstacle to the vertical tubes. The holes in the tubes are preferably of diameter between 2 and 6mm and are preferably disposed around the tube walls in a regular pattern eg a spiral or alternatively pointing inward and outward relative to the axis of the fermenter vessel.

Besides the above arrangement other geometrical arrangements of sparging systems may be used, for example spiral tubes or rings.

A preferred arrangement of the sparging system for use in a fermenter such as those described in UK Specification No. 1,353,008 and co-pending UK Applications Nos. 23330/73, 24266/75 and 52430/74 comprises a single main vertical tube located centrally within the fermenter riser and connected to a plurality of horizontal spargers through which the limiting nutrient is supplied to the culture. The spargers are located at a series of levels along the length of the main tube, there being a plurality of spargers at each level. When the riser contains baffles as described below the spargers are located in radial slots in the baffles thereby ensuring that the limiting nutrient is introduced into the culture in regions where there is a high velocity of flow due to the restriction in the cross-sectional area of the riser caused by the baffles.

Alternatively in a fermenter where the riser is an annulus surrounding the downcomer a similar arrangement of radial horizontal spargers can be used but their common supply will be ring-shaped or vertical tubes through which the limiting nutrient is pumped to individual spargers.

The risers of the fermenters of the UK Specification No. 1,353,008 and co-pending UK Applications Nos. 23330/73, 24266/75 and 52430/74 preferably contain series of baffles to control the flow of culture. These baffles may be for example at intervals of 1.2 meters in the riser. Preferably each baffle closes about five-sixths of the cross-sectional area of the riser leaving only one-sixth of the area open for culture to flow through. The open area may be distributed over a number of radial slots, eg 16, each of which may be bridged to close off half of its area thereby obtaining a reasonable slot width. When the slots are bridged this is done in a manner such that inner and outer open zones are created of equal or substantially equal area. The openings in the solid baffles need not be radial slots but can be openings of any shape provided that the baffle constrains the flow through the riser of the fermenter to a cross-sectional area small enough to achieve the required increase in velocity, suitably to a velocity above 1 meter/second. For example the openings in the baffles could be circular. In all cases it is preferred that the spargers are arranged to inject the limiting nutrient into the regions of high velocity flow through the baffle openings.

When, as in the fermenter of co-pending UK Application No. 52430/74, the riser is divided into sections one vertically above the other, said sections having different cross-sectional areas and forming a 'pot' and a 'spout' the baffles are installed in both sections.

Preferably the limiting nutrient is introduced into the fermenter in regions of high velocity flow, i.e., flow velocity greater than 1 meter/second. This can be done by introducing the limiting nutrient into the culture through injection nozzles or multiple nozzles such as spargers into the slots or other gaps in the baffles.

The apparatus of the invention is illustrated by the accompanying drawings wherein.

Figure 1:
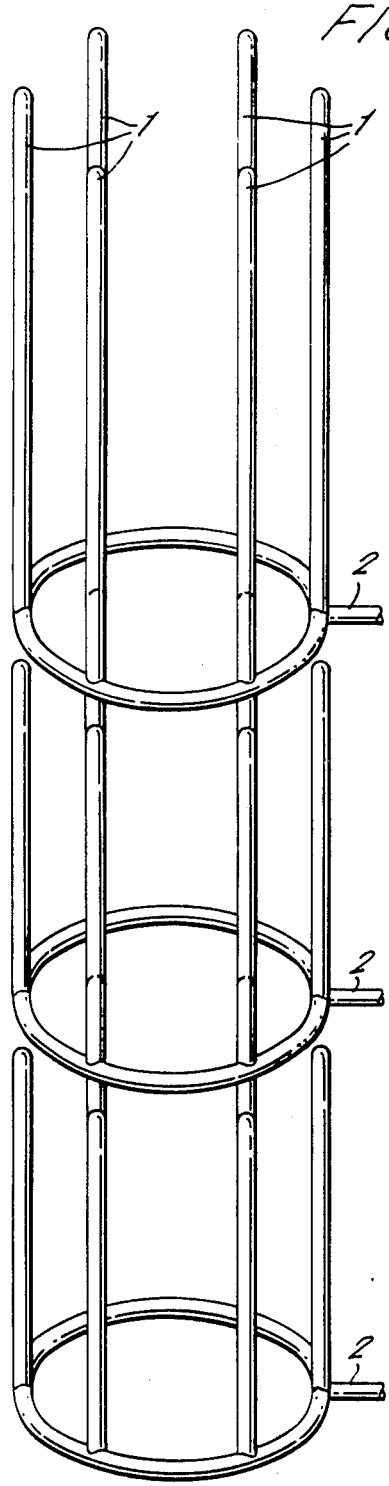
FIG. 1 is a perspective view of one arrangement.

The apparatus shown in FIG. 1 comprises six vertical medium distribution tubes 1 located at the corners of a regular hexagon and connected to three medium supply tubes 2 located at different levels along the heights of distribution tubes 1, the lowest supply tube being connected to the lower ends of distribution tubes 1. Each of supply tubes 2 comprises a circular portion connected to distribution tubes 1 with an outwardly extending portion which is connected to a medium supply (not shown in the drawing). Distribution tubes 1 and the circular parts of supply tubes 2 are perforated by a plurality of holes, (not shown in the drawing). These holes occur at intervals along the entire heights of distribution tubes 1 being closer together towards the lower ends of the tubes than at the upper ends, the vertical distance between successive holes increasing up the tubes. Successive holes are not located vertically above one another along the tubes 1 but are spaced around the circumference of the tubes forming a suitable pattern, eg a spiral. On the circular portions of supply tubes 2 holes are located at substantially equal horizontal distances apart and may also be distributed around the vertical section of the tube, eg by pointing alternatively inward and outward relative to the axis of the fermenter vessel.

Figure 2:
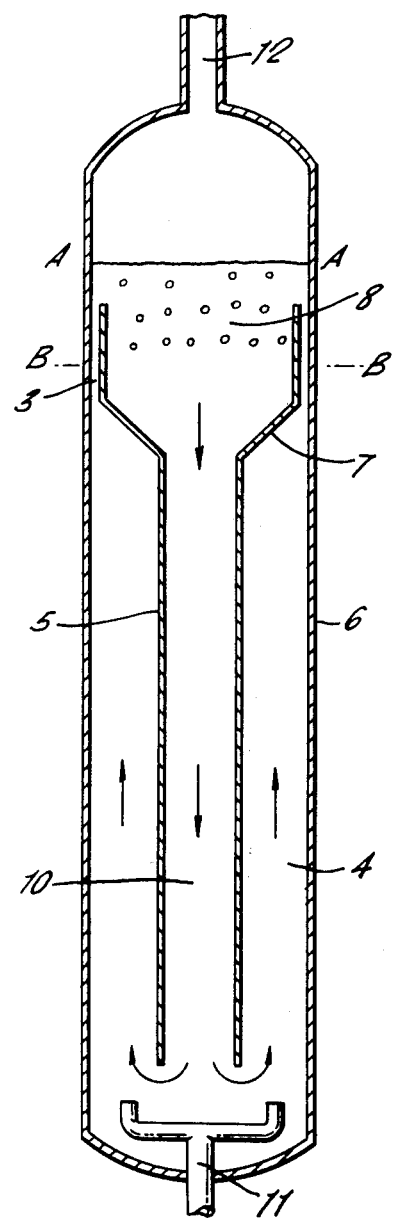
FIG. 2 is a diagrammatic representation of one fermenter in which the apparatus may be installed.
Figure 3:
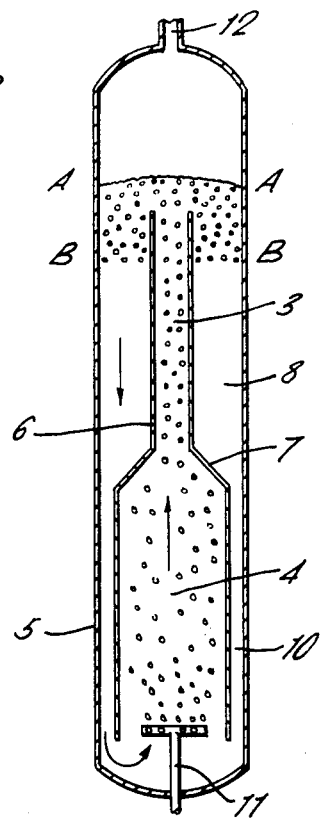
FIG. 3 is a diagramatic representation of a second fermenter in which the apparatus of the invention may be installed.

The fermenters shown in FIGS. 2 and 3 each have a riser 6 and a downcomer 5. In each case riser 6 is divided into two sections one vertically above the other, the lower section or 'pot' 4 being of greater cross-sectional area than the upper section or 'spout' 3. 'Pot' 4 and 'spout' 3 are linked by connecting piece 7. In each case downcomer 5 has two sections one vertically above the other, the upper section or 'choke' 8 being of greater cross-sectional area than the lower section or 'sink' 10.

'Spout' 3 opens into 'choke' 8 whilst the lower end of 'sink' 10 communicates with 'pot' 4. Air is sparged into the lower part of 'pot' 4 through spargers 11 causing culture contained in each fermenter to rise upwardly in the riser and to flow over into 'choke' 8 and thence pass into 'sink' 10. Culture fills each fermenter up to the level A—A, the region above level B—B in the 'choke' being occupied by bubbly culture. It is from the region above level B—B in 'choke' 8 that gas disengages from the culture to escape through port 12 at the upper end of each fermenter. The 'spout' 3 and 'choke' 8 and also the 'sink' 10 and 'pot' 4 are coaxially located. In the fermenter of FIG. 2 'spout' 3 surrounds 'choke' 8 and 'pot' 4 surrounds 'sink' 10 whilst in the fermenter of FIG. 3 the reverse is the case and the 'choke' and the 'sink' surround the riser 6.

Figure 4:
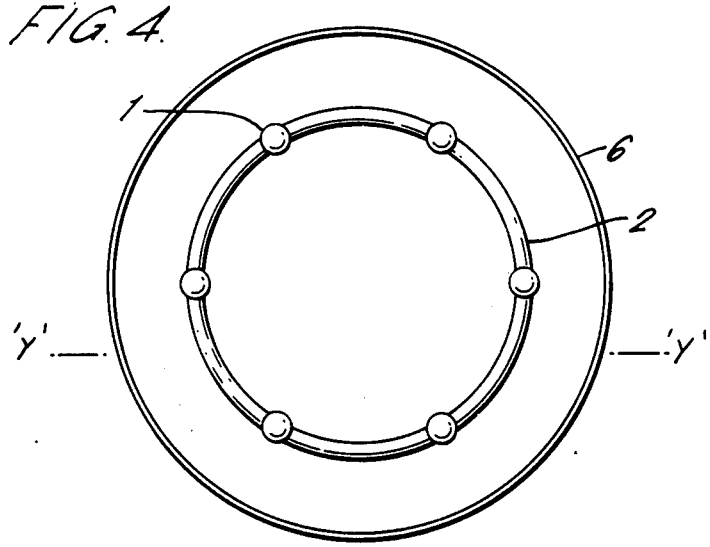
FIG. 4 is a plan view of the riser of the fermenter shown in FIG. 3 having the arrangement of FIG. 1 installed within it.
Figure 5:
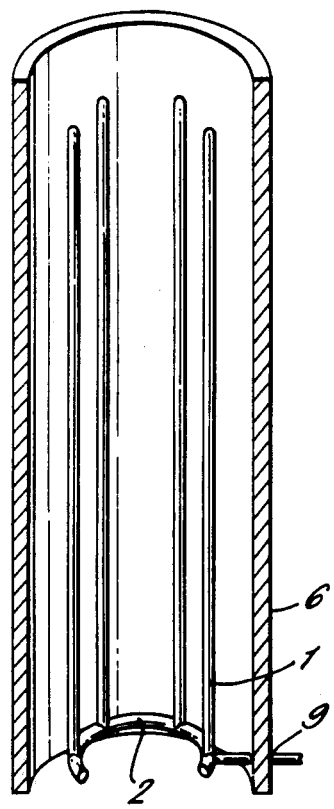
FIG. 5 is a sectional elevation along the line y-y of FIG. 4.

FIGS. 4 and 5 show part of riser 6 of the fermenter of FIG. 3 having an apparatus according to the invention installed within it. In this case the apparatus has only one supply tube which enters the fermenter at point 9.

During operation of a fermenter of FIG. 2 or FIG. 3 culture medium containing the carbon source and inorganic nutrients is supplied to the culture in riser 6 through supply tube 2 and distribution tubes 1 — passing into the culture through the holes in the supply tube 2 and distribution tubes 1 at substantially the same rate as culture is removed at a point or points not shown in the drawings.

Figure 7:
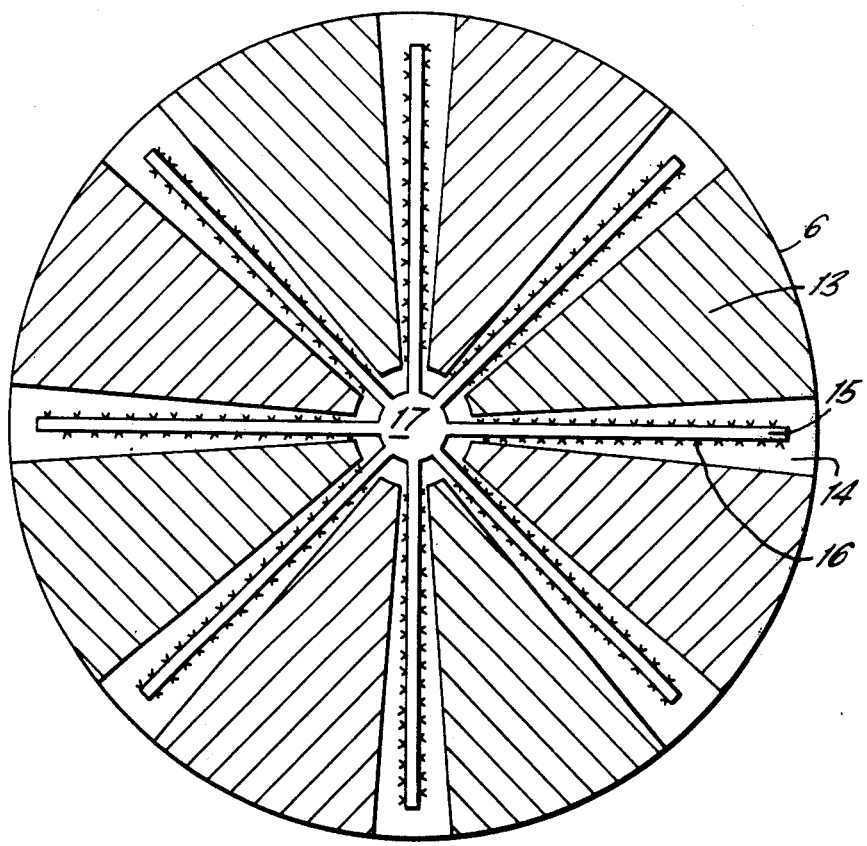
FIG. 7 is a cross-section through the riser of the fermenter shown in FIG. 3 fitted with baffles and having the preferred arrangement installed within it.

In the system shown in FIG. 7, riser 6 contains a series of layers of baffles 13 spaced apart vertically, each baffle being divided into segments by slots 14. The main vertical tube through which the limiting nutrient enters the fermenter is shown as 17 and is located centrally in riser 6. Spargers 15 radiate out from tube 17 at each baffle and are located in slots 14. Limiting nutrient passes from spargers 15 through holes 16 into the culture as it flows at increased velocity through slots 14.

Figure 6:
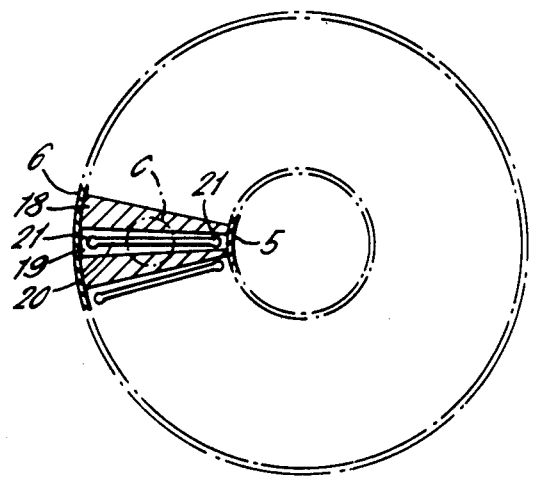
FIG. 6 is a cross-section through the fermenter shown in FIG. 2 fitted with baffles and having the preferred arrangement installed within it.
Figure 6A:
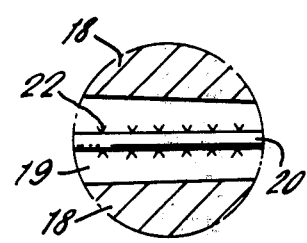
FIG. 6a is an enlarged view of the area within the circle C shown in FIG. 6.

In the system shown in FIGS. 6 and 6a riser 6 surrounds downcomer 5 and the geometrical arrangement of baffles and spargers differs from that shown in FIG. 7 because of this. However basically the systems are the same. That of FIGS. 6 and 6a contains a series of layers of baffles 18 spaced apart vertically, each baffle being divided into segments by slots 19. The limiting nutrient enters the fermenter through a plurality of vertical tubes 21, two of which pass through each slot 19, being connected in each slot by a sparger 20. Limiting nutrient passes from spargers 20 through holes 22 (shown in FIG. 6a) into the culture as it flows at increased velocity through slots 19.

In the systems shown in FIGS. 6 and 7 successive layers of baffles may be staggered with respect to one another as described in our co-pending UK Application No. 13559/74. In this case in the system shown in FIG. 6, vertical tubes 21 must be bent to accommodate the staggering of the layers of baffles.

I claim:

1. A method for the continuous fermentation of a culture comprising a nutrient medium, one of the constituents of which is a growth limiting nutrient, and microorganisms capable of utilizing the medium for growth wherein the growth limiting nutrient is supplied to the culture in an amount which corresponds stoichiometrically with the locally available supply of oxygen at an average of at least one position per cubic meter of the effective volume of a fermenter in which the fermentation is performed, said effective volume being the volume in which, through mass transfer from gas bubbles, a positive dissolved partial pressure of oxygen can be maintained, whereby substantially all the limiting nutrient supplied at each position is consumed by the microorganisms present in the culture in the vicinity of that position before oxygen nutrient available to them in the culture in the vicinity of that position is exhausted and becomes the limiting nutrient.

2. A method according to claim 1 wherein the limiting nutrient is a carbon source assimilable by the microorganisms.

3. A method according to claim 2 wherein the microorganisms are selected from the group consisting of methanol utilizing strains of bacteria of the species *Pseudomonas methylotropha, Microcyclus polymorphum, Hyphomicrobium variabile* or *Pseudomonas rosea* and the limiting nutrient is methanol.

4. A method according to claim 3 wherein the amount of methanol supplied at any position does not exceed 15 l/hr.

5. A method according to claim 1 wherein the limiting nutrient is supplied at a velocity above 3 meters/sec.

* * * * *